(12) United States Patent
Pomerantz (10) Patent No.: US 8,906,690 B2
(45) Date of Patent: Dec. 9, 2014

(54) METHODS FOR SIMULTANEOUS ESTIMATION OF QUANTITATIVE MINEROLOGY, KEROGEN CONTENT AND MATURITY IN GAS SHALE AND OIL-BEARING SHALE

(75) Inventor: Andrew E. Pomerantz, Lexington, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 314 days.

(21) Appl. No.: 13/446,975

(22) Filed: Apr. 13, 2012

(65) Prior Publication Data

US 2013/0273661 A1 Oct. 17, 2013

(51) Int. Cl.
*G01N 33/24* (2006.01)
*G01N 21/35* (2014.01)

(52) U.S. Cl.
USPC .............. 436/29; 436/31; 436/164; 436/171; 436/174

(58) Field of Classification Search
CPC .......... G01J 3/42; G01N 1/286; G01N 21/35; G01N 21/3563; G01N 21/55; G01N 21/59; G01N 21/65; G01N 33/24; G01N 33/241; G01N 2001/286; G01N 2001/2866; G01N 2021/3563; G01N 2021/3572; G01N 2021/3595; G01N 2033/94
USPC .............................. 436/29, 31, 164, 171, 174
See application file for complete search history.

(56) References Cited

U.S. PATENT DOCUMENTS

| | | | | |
|---|---|---|---|---|
| 4,321,465 | A * | 3/1982 | Stover et al. | 250/255 |
| 4,839,516 | A * | 6/1989 | Freeman et al. | 250/255 |
| 4,911,001 | A * | 3/1990 | Ferguson | 73/863 |
| 5,082,787 | A * | 1/1992 | Nolte et al. | 436/31 |
| 5,161,409 | A | 11/1992 | Hughes et al. | |
| 5,306,909 | A | 4/1994 | Jones et al. | |
| 5,939,717 | A * | 8/1999 | Mullins | 250/255 |
| 7,167,742 | B2 * | 1/2007 | Camacho et al. | 600/473 |
| 7,379,819 | B2 | 5/2008 | Betancourt et al. | |
| 2007/0159625 | A1 * | 7/2007 | DiFoggio | 356/328 |
| 2008/0030729 | A1 * | 2/2008 | DiFoggio | 356/328 |
| 2012/0153160 | A1 * | 6/2012 | Forrester et al. | 250/341.8 |
| 2012/0226653 | A1 * | 9/2012 | McLaughlin et al. | 706/52 |
| 2013/0046469 | A1 * | 2/2013 | Herron et al. | 702/2 |
| 2013/0269933 | A1 * | 10/2013 | Pomerantz et al. | 166/264 |
| 2013/0270011 | A1 * | 10/2013 | Akkurt et al. | 175/58 |

OTHER PUBLICATIONS

Rouxhet, P. G. et al, Fuel 1978, 57, 533-540.*
Solomon, P. R. et al, Fuel 1980, 59, 893-896.*
Cronauer, D. C et al, "Characterization of oil shale by FTIR spectroscopy" ACS division of Fuel Chemistry Proceedings, "Symposium on Processing of Oil Shale Tar Sands and Heavy Oils" Meeting 183, Las Vegas, NV, 27(2) 1982,122-130. http://pubs.acs.org/cgi-bin/preprints/display?div=fuel&meet=183&page=27_2_LAS VEGAS_03-82_0122.pdf.*
Schenk, H. J. et al, Organic Geochemistry 1986, 10, 1099-1104.*
Udo, O. T. et al, Journal of Geochemical Exploration 1990, 37, 285-300.*
Kister, J. et al, Fuel, 1990, 69, 1356-1361.*
Ganz, H. H. et al, Journal of Southeast Asian Earth Sciences 1991, 5, 19-28.*
Requejo, A. G. et al, Energy & Fuels 1992, 6, 203-214.*
Lin, R. et al, Applied Spectroscopy 1993, 47, 265-271.*
Barth, T. et al, Organic Geochemistry 1995, 23, 139-158.*
Landais, P., Organic Geochemistry 1995, 23, 711-720.*
Ballice, L. et al, Fuel 1995, 74, 1618-1623.*
Borrego, A. G. et al, Organic Geochemistry 1996, 24, 309-321.*
Kruge, M. A. et al, Energy & Fuels 1997, 11, 503-514.*
Ruau, O. et al, Fuel 1997, 75, 645-653.*
Akande, S. O. et al, Organic Geochemistry 1998, 29, 531-542.*
Lis, G. P. et al, Organic Geochemistry 2005, 36, 1533-1552.*
Breen, C. et al, Journal of Petroleum Science and Engineering 2008, 60, 1-17.*
Vogel, H. et al, Journal of Paleolimnology 2008, 40, 689-702.*
Herron, M. M. et al, 28th Oil Shale Symposium, Colorado School of Mines 2008, 1-8.*
Rosen, P. et al, Environmental Science & Technology 2011, 45, 8858-8865.*
Wang, S. et al, Energy & Fuels 2011, 25, 5672-5677.*
International search report for the equivalent PCT patent application No. PCT/US2013/035868 issued on Jul. 8, 2013.
M. Herron, A. Matterson, G. Gustayson "Dual Range FT-IR Mineralogy and the Analysis of Sedimentary Formations," The Proceedings of the 1997 International Symposium of the Society of Core Analysts, Calgary, Sep. 7-10, Paper SCA-9729.

* cited by examiner

*Primary Examiner* — Arlen Soderquist
(74) *Attorney, Agent, or Firm* — Stephanie Chi (57) ABSTRACT

A method for estimating characteristics of a formation including collecting a formation sample, preparing the sample, and analyzing the sample using FTIR comprising identifying the kerogen lineshape and intensity. The method includes using the lineshape to obtain kerogen maturity, using the maturity to obtain the kerogen spectrum, and using the kerogen spectrum to obtain the mineralogy and kerogen content.

15 Claims, 7 Drawing Sheets
(5 of 7 Drawing Sheet(s) Filed in Color)

METHODS FOR SIMULTANEOUS ESTIMATION OF QUANTITATIVE MINEROLOGY, KEROGEN CONTENT AND MATURITY IN GAS SHALE AND OIL-BEARING SHALE

FIELD

This application relates to methods and apparatus to provide information for the recovery of hydrocarbons. Specifically, embodiments described herein collect information and manipulate it to efficiently estimate the mineralogy, kerogen content and maturity of a sample.

BACKGROUND

Measurements have historically been made on cutting sample or core samples either in the field or in the laboratory. Estimating mineralogy of conventional rocks (containing no hydrocarbon) using FTIR is an established technique. In this measurement, a library of spectra of standard minerals is recorded first, and then the spectrum of a rock is fitted to a linear combination of standards, with the fitted weights proportional to the abundance of each mineral. In favorable cases, this procedure can be extended to produce a simultaneous measurement of mineralogy and kerogen content by recording the spectrum of a standard kerogen and adding that to the library of standard spectra; for example, mineralogy and kerogen content have been measured in sediments using diffuse reflection FTIR data and in Green River oil shales using transmission FTIR data following this procedure.

Figure 1:
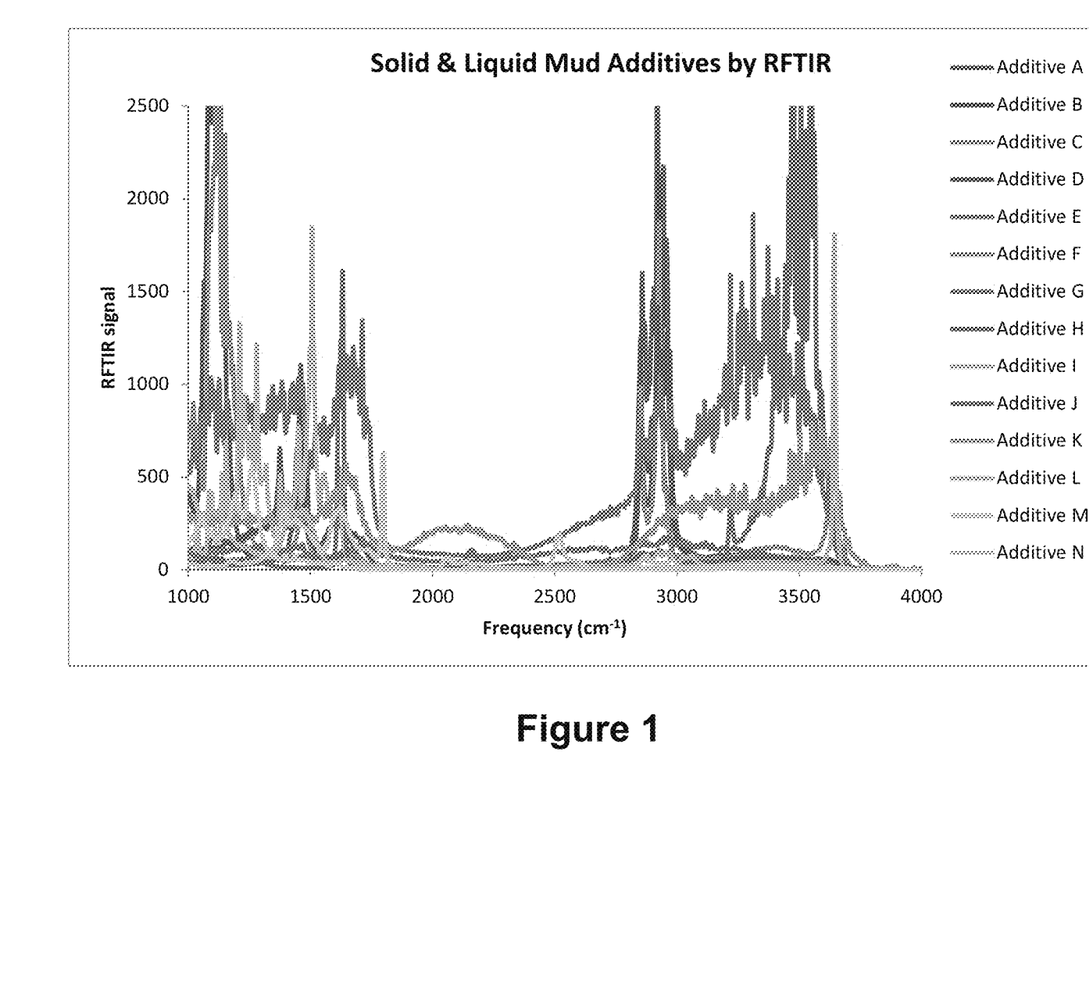
FIG. 1 is an FTIR plot illustrating how the presence of additives may distort results.

Limited information has been collected by FTIR or visual inspection of formation solids under a microscope, especially cuttings with residual drilling mud solvents. More involved analysis have not been selected because of the time and cost for equipment and low likelihood of return of useful information. For example, FIG. 1 shows how an FTIR analysis may be distorted by the presence drilling mud fluids. Also, core samples may undergo more sophisticated analysis, and core samples do not have the same exposure to drilling fluids that cuttings samples undergo.

Separately, some references have methods based on interpreting variations in the FTIR spectra of kerogens from gas shales and oil-bearing shales to estimate properties of the kerogen. The properties typically measured are the kerogen type (reflecting the organic material from which the kerogen was formed) and maturity (reflecting the extent of alteration of the kerogen due to thermal processes). However, those methods require isolating the kerogen from the rock, typically by digesting the minerals using acid. Therefore, those methods provide no estimate of mineralogy.

SUMMARY

Embodiments relate to a method for estimating characteristics of a formation collecting a formation sample, preparing the sample, and analyzing the sample using FTIR comprising identifying the kerogen lineshape and intensity. The method includes using the lineshape to obtain kerogen maturity, using the maturity to obtain the kerogen spectrum and using the kerogen spectrum to obtain the mineralogy and kerogen content.

FIGURES

The patent or application file contains at least one drawing executed in color. Copies of this patent or patent application publication with color drawing will be provided by the Office upon request and payment of the necessary fee.

DESCRIPTION

At the outset, it should be noted that in the development of any such actual embodiment, numerous implementation-specific decisions must be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary of the invention and this detailed description, each numerical value should be read once as modified by the term "about" (unless already expressly so modified), and then read again as not so modified unless otherwise indicated in context. Also, in the summary of the invention and this detailed description, it should be understood that a concentration range listed or described as being useful, suitable, or the like, is intended that any and every concentration within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that inventors appreciate and understand that any and all data points within the range are to be considered to have been specified, and that inventors possessed knowledge of the entire range and all points within the range.

The statements made herein merely provide information related to the present disclosure and may not constitute prior art, and may describe some embodiments illustrating the invention.

Definitions

The reservoir quality (hereafter RQ) is defined by a number of petrophysical and hydrocarbon properties (e.g., porosity, permeability, total organic content versus total inorganic content and maturation, hydrocarbon content and type, gas sorption mechanisms) defining reservoir potential.

The completion quality (CQ) depends on the poromechanical properties of the field and reservoir, which means the conditions that are favorable to the creation, propagation and containment of hydraulic fractures, as well as the placement of proppant and retention of fracture conductivity. It depends mainly on the intrinsic geomechanics properties, i.e. in situ stress field, pore pressure, material properties (elastic, yield or quasi-brittle failure, hardness, rock-fluid sensitivity), their anisotropic nature and their spatial heterogeneities, as well as the presence of discontinuities (such as natural fractures or geological layering) and the orientation of the well. SPE 144326 provides more information for the definitions of RQ and CQ and is incorporated by reference herein.

Further, as a well is being drilled, the rock that is undergoing the drilling is cut or otherwise fragmented into small pieces, called "cuttings" that are removed from the bulk of the formation via drilling fluid. The process is similar to drilling a hole in a piece of wood which results in the wood being cut into shavings and/or sawdust. Cuttings are representative of the reservoir rock—although they have been altered by the drilling process, they still may provide an understanding of the reservoir rock properties. This is often referred to as "mud logging" or "cuttings evaluation." For effective logging or evaluation as described below, the cuttings are prepared by removing residual drilling fluids.

Staging is the design of the locations of the multiple hydraulic fracturing stages and/or perforation clusters.

The term "unconventional" is used refer to a formation where the source and reservoir are the same, and stimulation is required to create production.

The "source" aspect implies that the formation contains appreciable amounts of organic matter, which through maturation has generated hydrocarbons (gas or oil, as in Barnett and Eagle Ford, respectively).

The "reservoir" aspect signifies that the hydrocarbons have not been able to escape and are trapped in the same space where they were generated. Such formations have extremely low permeabilities, in the order of nanodarcies, which explains why stimulation in the form of hydraulic fracturing is needed.

Bitumen and kerogen are the non-mobile, organic parts of shales. Bitumen is defined as the fraction that is soluble in a solvent (typically a polar solvent such as chloroform or a polarizable solvent such as benzene). Kerogen is defined as the fraction that is insoluble.

Rock cores are reservoir rocks collected with a special tool that produces large samples with little exposure to drilling fluids.

Demineralizing refers to the process of removing the mineral components of formation sample to result in a higher concentration kerogen containing material. An example of demineralization is an acid attack.

While historical methods for estimate mineralogy and kerogen content in unconventionals using FTIR have provided some information, they are unlikely to be as successful generally for the following reason: estimating the content of a particular species (kerogen or mineral) in a rock using FTIR requires that the spectrum of that species in the in the library of standards is representative of the corresponding spectrum of that species in the rock. The spectrum of a typical mineral is essentially the same regardless of where that mineral was collected (consistent with the definition of a mineral as having a characteristic chemical composition), and the same is true for kerogen in sediments; thus it is typically the case that the standard spectra of minerals and sediment kerogen are representative. However, it is known that the spectrum of kerogen from gas shales and oil-bearing shales is not constant; for example, the FTIR spectra of kerogens from gas shales and oil-bearing shales contain a feature near 2,900 cm-1, and the intensity of that feature can vary by an order of magnitude among kerogens from the same basin and by two orders of magnitude among kerogens from different basins. Therefore, simple extension of the established technique requires the assumption that a single kerogen standard spectrum can be considered representative for all shale samples in the study set; that assumption can be poor in gas shales and oil-bearing shales, limiting the accuracy of the results based on that technique. Additionally, results based on this technique provide no estimate of maturity.

Reservoir Quality and Completion Quality Generally

Formation evaluation in gas shale and oil-bearing shale reservoirs involves estimation of quantities such as mineralogy, kerogen content and thermal maturity (reflecting the extent of alteration of the kerogen due to thermal processes). These quantities are important for estimating the reservoir quality and completion quality of the formation, and measurement of these quantities as a function of depth is desirable in nearly every well in shale plays. Embodiments herein provide a procedure for estimating all three of these quantities simultaneously. The procedure involves the use of infrared spectroscopy, for example infrared spectroscopy recorded using a Fourier transform technique (FTIR) as is commonly used for estimating mineralogy in conventional rocks that have been cleaned of hydrocarbons. These measurements can be performed using FTIR spectra recorded in diffuse reflection mode, transmission mode, photoacoustic mode, Raman mode, and/or with a diamond-window compression cell.

Embodiments described herein fully exploit the data that may be collected using cuttings and/or core samples, drilling operation data, pressure tests, gamma ray feedback, and/or other methods to estimate reservoir quality and completion quality. Characterization of the mineral (inorganic) and non-mineral (organic) content of formation samples is the objective including weight fractions of inorganic and organic content, total organic content (TOC), and/or mineralogy. Additional information may be obtained via U.S. patent application Ser. No. 13/447,019 (now U.S. Patent Publication 2013/0270011) filed Apr. 13, 2012 entitled RESERVOIR AND COMPLETION QUALITY ASSESSMENT IN UNCONVENTIONAL (SHALE GAS) WELLS WITHOUT LOGS OR CORE, by Ridvan Akkurt, Romain Charles Andre Priol, and Andrew E. Pomerantz; which is incorporated by reference herein.

Cuttings Preparation

Drilling rock cuttings flow from the drill bit to the surface of the well through the circulated drilling mud. The cuttings may be analyzed to estimate the volume of inorganic minerals and organic matter (e.g., TOC) as well as the porosity. Cuttings samples preparation often historically involves collecting material from a shale shaker, additional sorting via a small hand held sieve, rinsing the material with the drilling fluid base oil, and then exposing the material to hexane. The hexane and other volatile organic material are baked out of the sample in an oven at 80° C. Soap and water may also be used to remove residual base oil.

Embodiments of the invention may use a procedure designed to prepare shale cuttings drilled with oil-based drilling fluid for analysis by FTIR and gas sorption. Details for an effective process are provided in U.S. patent application Ser. No. 13/446,985 (now U.S. Patent Publication 2013/0269933, filed Apr. 13, 2012, entitled METHOD AND APPARATUS TO PREPARE DRILL CUTTINGS FOR PETROPHYSICAL ANALYSIS BY INFRARED SPECTROSCOPY AND GAS SORPTION, which is incorporated by reference herein. In some embodiments, preparing a sample includes exposing the sample to a cleaning fluid that may contain a surfactant. Some embodiments may crush the sample to a diameter of about 10 micron.

After completing these steps, the cuttings are sufficiently clean, have the correct particle size and have retained their kerogen and bitumen. They are now ready for FTIR and gas sorption analysis. Some embodiments do not include exposing the sample to acid and demineralizing does not occur.

Simultaneous Estimation of Maturity, Kerogen Content and Mineralogy Via FTIR

Embodiments provide a way to estimate mineralogy, kerogen content and maturity of a gas shale or oil-bearing shale from a single FTIR measurement. The workflow involves analyzing a spectral feature near 2,900 cm-1 to estimate the maturity of the kerogen. That information on maturity is used to define a representative kerogen standard spectrum. That kerogen standard is then added to the library of standards, and the FTIR spectrum of this particular sample is fitted to a linear combination of the library of standards, with the fitted weights providing a quantitative estimate of mineralogy and kerogen content. Therefore, this workflow provides a simultaneous and accurate estimate of mineralogy, kerogen content and maturity.

This interpretation can be applied on rock samples, including core and cleaned cuttings. It can be performed in the laboratory or at the well-site. It uses vibrational spectra, and those spectra can be recorded as infrared spectra in Fourier transform mode (FTIR), transmission mode, reflectance mode, photoacoustic mode, or with a diamond-window compression cell or as Raman spectra in similar modes.

Figure 2:
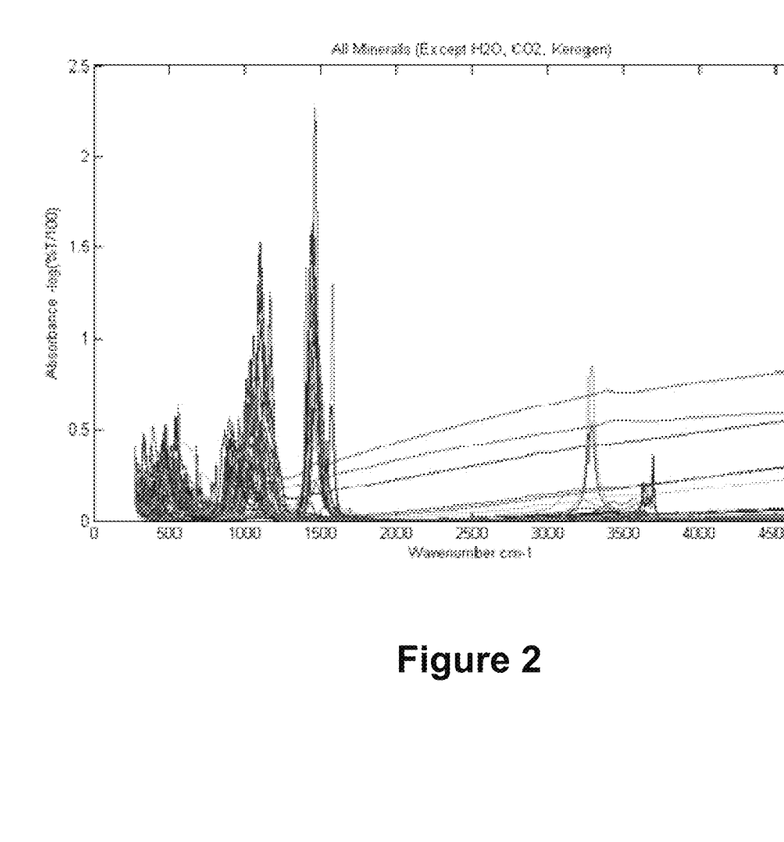
FIG. 2 is an FTIR plot of spectra of nearly 100 mineral standards recorded in transmission mode.
Figure 3:
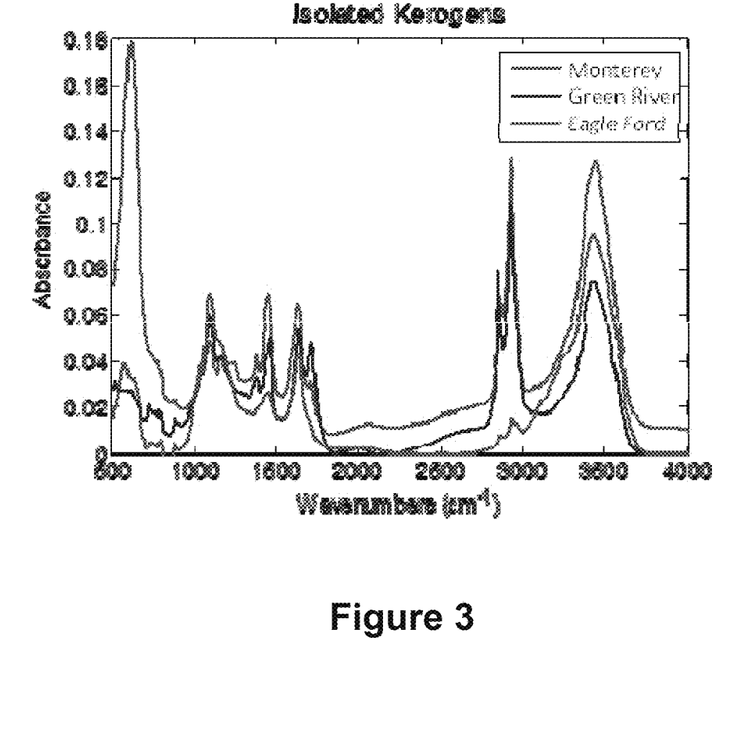
FIG. 3 is FRIR spectra of three kerogen standards.

The workflow for simultaneously and accurately estimating mineralogy, kerogen content and maturity in a gas shale or oil-bearing shale from infrared spectroscopy is as follows:

1. Collect a sample of rock. The sample can be either core or cleaned cuttings.
2. Measure the infrared spectrum of the rock. The spectral range should be approximately 400-4,000 cm$^{-1}$. This measurement can be performed in the laboratory or at the well-site. The measurement can be conducted in transmission mode, reflectance mode, photoacoustic mode, or with a diamond-window compression cell. Any equipment that provides traditional FTIR measurement will provide an effective measurement. The VERTEX 70/70v FT-IR™ spectrometer, commercially available from Bruker Optics of Billerica, Mass. may be selected for some embodiments.
3. Analyze the lineshape of the peaks at 2,900 cm-1, and from that analysis estimate the maturity of the kerogen. Much of the FTIR spectral range consists of peaks from both minerals and kerogen. However, there is a window near 2,900 cm-1 where the absorption from minerals typically is weak while the absorption from kerogen is strong. For example, FIG. 2 shows the transmission FTIR spectra of nearly 100 minerals standards, demonstrating the weak absorption near 2,900 cm-1. On the other hand, FIG. 3 shows the FTIR spectra of three kerogen standards, and for two of them that region contains the most intense feature in the spectrum. Because that region contains kerogen absorption with little background from mineral absorption, the lineshape of that feature can be analyzed in detail to provide further information on the kerogen, without interference from minerals.

Figure 4:
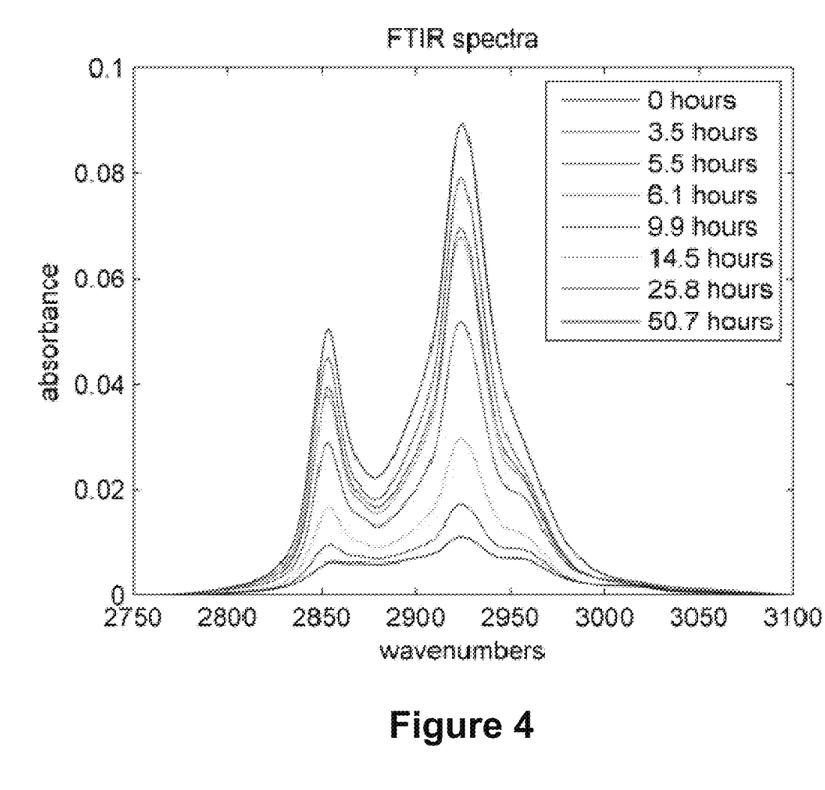
FIG. 4 FTIR sprectra of Green River shale samples matured in the lab.
Figure 5:
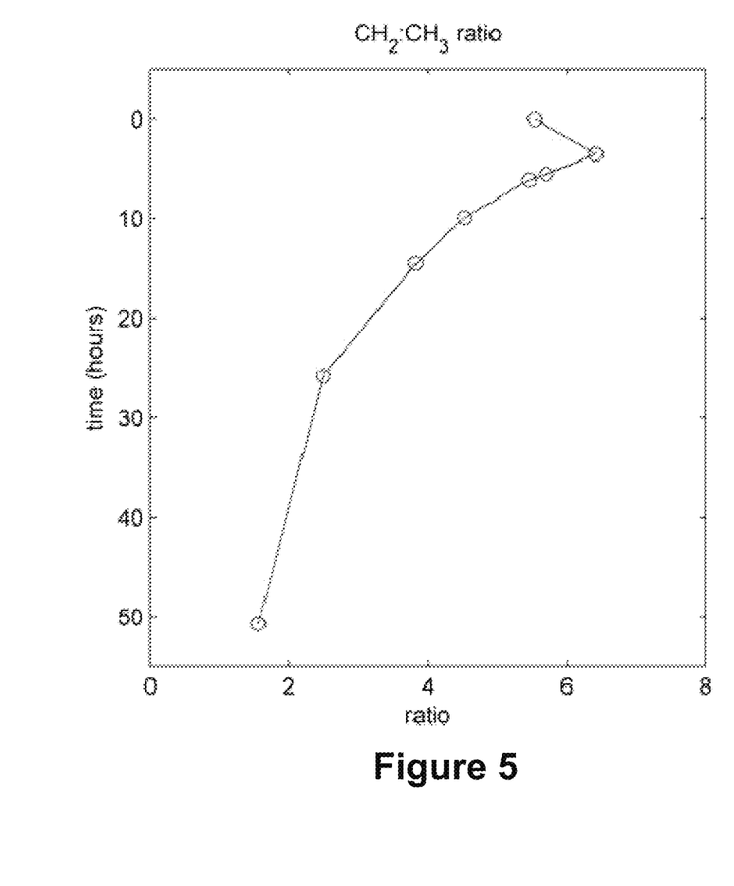
FIG. 5 is the chemical composition of kerogen as measutre by FTIR, correlating with maturity.

The spectra feature near 2,900 cm-1 is composed of five partially resolved transitions: $CH_2$ symmetric stretching centered near 2849 cm-1, $CH_3$ symmetric stretching centered near 2864 cm-1, CH stretching centered near 2891 cm-1, $CH_2$ asymmetric stretching centered near 2923 cm-1, and $CH_3$ asymmetric stretching centered near 2956 cm-1. Analyzing the lineshape of that feature—for example fitting that feature to linear combination of five peaks (one peak for each transition mentioned above)—provides information about the relative abundance of CH, $CH_2$, and $CH_3$ chemical groups in the kerogen. The abundance of those groups varies in a systematic way with the maturity of the kerogen, as shown in FIG. 4 and FIG. 5. FIG. 4 shows the FTIR spectra (near 2,900 cm-1) of Green River shales that have been subject to maturation in the laboratory for various amounts of time (longer periods of time correspond to more mature kerogen). It is clear that the shape of those spectra vary significantly with maturity. Samples are labeled according to the duration of laboratory maturation.

In particular, FIG. 5 shows the $CH_2$:$CH_3$ ratio obtained by fitting the spectra to five peaks as described above. The figure demonstrates that the $CH_2$:$CH_3$ ratio varies systematically with kerogen maturity. Therefore, by examining the lineshape of the feature near 2,900 cm-1, the maturity of the kerogen can be estimated.

Figure 6:
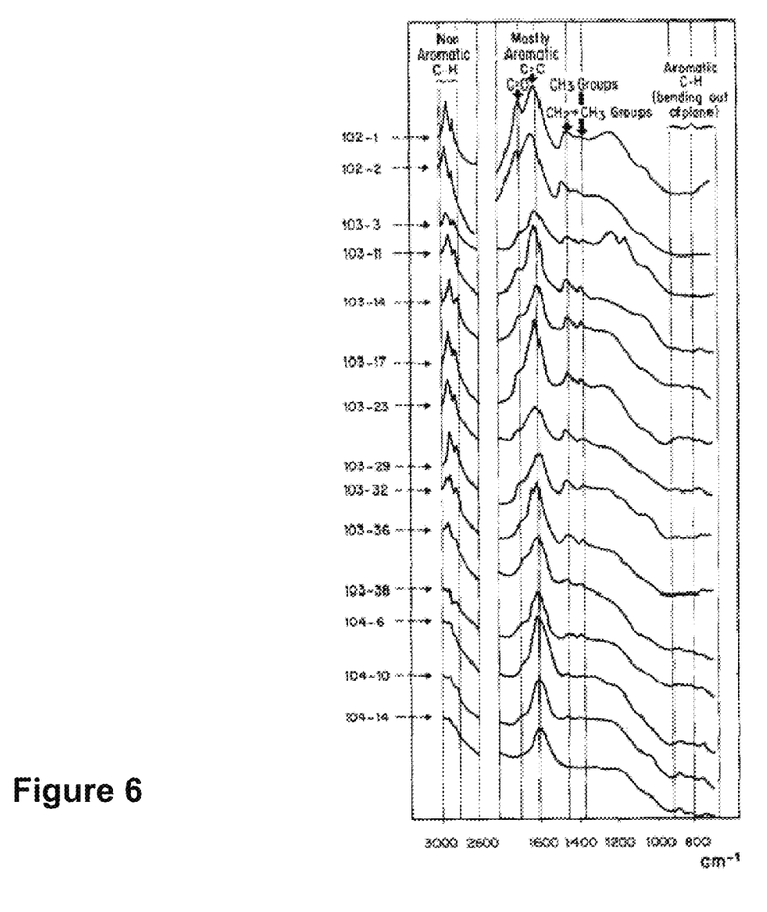
FIG. 6 is a plot of kerogen spectra from multiple depths in the same basin.

4. From the now known maturity, define a kerogen standard. As shown in the step above, the lineshape of the feature near 2,900 cm-1 varies with maturity. In addition, the intensity of that peak also varies with maturity. For example, FIG. 6 shows a plot (reproduced from Durand, 1976) of the spectra of a series of kerogens collected from different depths in the same well. The y-axis shows the depth, with higher numbers (closer to the origin) indicating more mature samples. The spectra in the region 2,600-3,000 cm$^{-1}$ show a sloping baseline (which results from scattering and can be eliminated with now known techniques) and the absorption peak near 2,900 cm-1. For more mature samples, the peak is less intense. Deeper depths correspond to more mature samples and have less intense features at 2,900 cm$^{-1}$.

Figure 7:
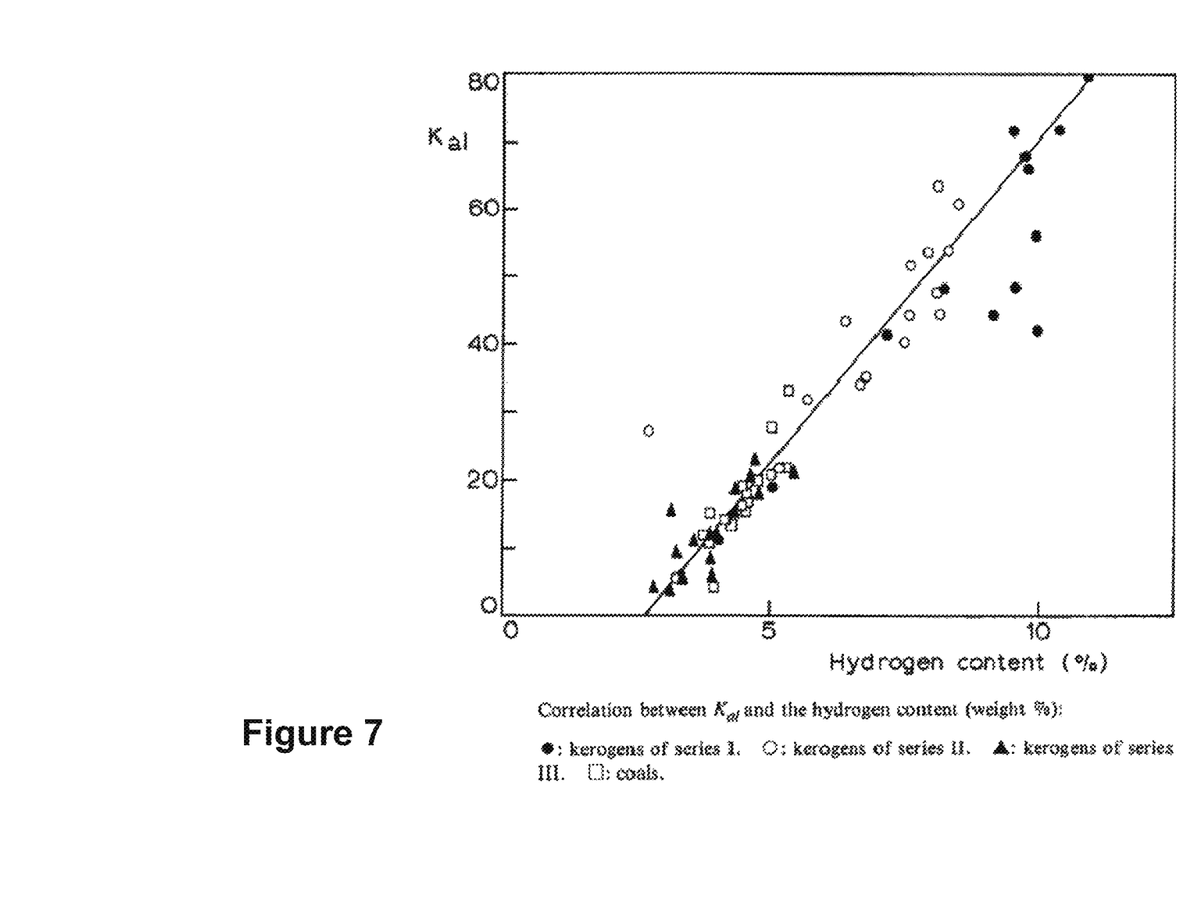
FIG. 7 is a plot of Kal reproduced from Rouxhet, 1980, providing intensity of the spectral feature near 2,900 cm-1 as a function of the hydrogen content of various kerogens.

Another example of the same effect is shown in FIG. 7, reproduced from Rouxhet, 1980. Here the y-axis indicates the intensity of the spectral feature at 2,900 cm-1 per unit mass of kerogen. The x-axis represents the hydrogen content of the kerogen, which is a measure of maturity (the hydrogen content decreases in kerogens of increased maturity, as is well-known from the Van Krevelen diagram). The figure again demonstrates that the intensity of the peak near 2,900 cm-1 decreases with maturity.

Thus, for a particular shale sample, from the maturity (provided in step #3) it is possible to estimate the relationship between the FTIR spectrum (intensity of the feature near 2,900 cm-1) and the mass of kerogen, using a relationship such as shown in FIG. 6 and FIG. 7. That relationship between the spectrum and the mass of material is the standard spectrum.

5. With the kerogen standard now defined, invert the full FTIR spectrum to yield quantitative mineralogy and kerogen content. That is, with a kerogen standard now added to the library of mineral standards, the full spectrum of the shale can be inverted. The mineralogy parameters observed here are the abundances (typically reported as mass fraction) of each of a several minerals or groups of minerals. Typically several dozen minerals are quantified. Clastics, clays, and carbonate minerals are routinely quantified using FTIR.

Inversion can involve any of the processes known in the art, including partial least squares, wavelet transform and Beer's law. The FTIR spectrum of a rock is inverted using a library of standards including minerals and kerogen in some emboidments. Additional information is available in The Proceedings of the 1997 International Symposium of the Society of Core Analysts, Calgary, September 7-10, Paper SCA-9729, "Dual Range FT-IR Mineralogy and the Analysis of Sedimentary Formations," by Michael Herron, Abigail Matteson, and Gale Gustayson, which is incorporated by reference herein.

This process can be implemented in one of two ways. First, FIG. 6 shows the spectra of kerogens of various maturities. In principle, any of the spectra could be selected to represent the kerogen standard for a sample of interest, but given the variation between the spectra, large errors would result if the wrong spectrum was selected. Using the maturity information, the most appropriate spectrum from FIG. 6 could be selected by choosing the spectrum from FIG. 6 corresponding to the maturity that is closest to the maturity of the sample of interest. That spectrum is then added to the library of standards. With an appropriate kerogen standard now in the library, the full spectrum could be inverted in the traditional manner to yield quantitative mineralogy and kerogen content.

Second (an alternative method of accomplishing the same goal), the intensity of the feature near 2,900 cm-1 could be determined and because the relationship between that intensity and the kerogen mass is known from step #4, the kerogen content can be estimated. Quantitative estimates of mineralogy then result from inverting the region of the spectrum away from 2,900 cm-1 in the traditional manner. Simple corrections based on subtracting an approximate kerogen spectrum from the region away from 2,900 cm-1 (to more accurately estimate mineralogy) or on subtracting an approximate mineral spectrum from the region near 2,900 cm-1 (to more accurately estimate kerogen content and maturity) are obvious extensions of this procedure.

In some embodiments, analyzing the sample occurs in less than 24 hours. In some embodiments the analyzing occurs before recovering hydrocarbons begins. Analyzing occurs after producing hydrocarbons begins in some embodiments and during reservoir characterization during production in some embodiments. Some embodiments use equipment within 500 meters of a wellbore.

I claim:

1. A method for estimating characteristics of a formation, comprising:
   (a) collecting and preparing a subterranean rock formation sample, wherein the preparing yields a non-demineralized formation sample;
   (b) measuring a Fourier transform infrared (FTIR) spectrum of the non-demineralized formation sample prepared in (a);
   (c) analyzing a spectral feature of the FTIR spectrum measured in (b) in a window including 2900 $cm^{-1}$ to obtain an estimate of a maturity of kerogen in non-demineralized formation sample prepared in (a);
   (d) defining a representative kerogen standard spectrum from the maturity of kerogen estimated in (c); and
   (e) inverting the infrared spectrum measured in (b) using the representative kerogen standard spectrum defined in (d) to yield a quantitative mineralogy and a kerogen content of the non-demineralized formation sample prepared in (a) such that the kerogen maturity, kerogent content, and quantitiative mineralogy of the sample are obtained from a single FTIR measurement.

2. The method of claim 1, wherein (c) further comprises fitting the spectral feature to a combination of the following peaks: (i) a $CH_2$ symmetric stretching centered at about 2849 $cm^{-1}$, (ii) a $CH_3$ symmetric stretching centered at about 2864 $cm^{-1}$, (iii) a CH stretching centered at about 2891 $cm^{-1}$, (iv) a $CH_2$ asymmetric stretching centered at about 2923 $cm^{-1}$, and (v) a $CH_3$ asymmetric stretching centered at about 2956 $cm^{-1}$ to obtain an estimate of a $CH_2:CH_3$ ratio in the kerogen, the ratio being indicative of the kerogen maturity.

3. The method of claim 1, where the representative kerogen spectrum defined in (d) is added to a library of mineral spectra.

4. The method of claim 3, where the inverting in (e) comprises fitting the FTIR spectrum measured in (b) to the library of standards, such that fitting weights provide a quantitative estimate of the mineralogy and the kerogen content.

5. The method of claim 1, wherein the inverting in (e) comprises the use of partial least squares, wavelet transform, or Beer's law.

6. The method of claim 1, wherein the subterranean rock formation sample is exposed to a cleaning fluid in (a).

7. The method of claim 6, wherein the cleaning fluid comprises a surfactant.

8. The method of claim 1, wherein (a) further comprises crushing the sample to a diameter of about 10 micron.

9. The method of claim 1, wherein (a) through (e) occur in less than 24 hours.

10. The method of claim 1, wherein (a) through (e) occurs before recovering hydrocarbons begins.

11. The method of claim 1, wherein (a) through (e) make use of equipment within 500 meters of a wellbore.

12. The method of claim 1, wherein (a) through (e) occurs while drilling the formation.

13. The method of claim 1, wherein the subterranean rock formation sample is a core sample.

14. The method of claim 1, wherein the subterranean rock formation sample is a solid collected from a drilling operation.

15. The method of claim 1, wherein the preparing in (a) does not include exposing the sample to acid.

* * * * *